United States Patent [19]

McAndrew

[11] Patent Number: 5,991,696
[45] Date of Patent: Nov. 23, 1999

[54] METHOD FOR INTELLIGENT DATA ACQUISITION IN A MEASUREMENT SYSTEM

[75] Inventor: James J. F. McAndrew, Lockport, Ill.

[73] Assignee: American Air Liquide Inc., Walnut Creek, Calif.

[21] Appl. No.: 08/893,539

[22] Filed: Jul. 11, 1997

[51] Int. Cl.⁶ ............................ G01N 7/00; G01N 21/31
[52] U.S. Cl. ..................... 702/24; 73/23.2; 73/31.06; 250/339.13; 250/339.1; 356/326
[58] Field of Search ................... 702/24; 73/23.2, 73/31.06, 40.05 R; 95/8; 438/14; 250/339.11, 339.13, 339.1, 341.4, 343; 340/632; 356/326, 433, 437, 439; 436/146, 151, 171, 174, 153, 167

[56] References Cited

U.S. PATENT DOCUMENTS

| | | | |
|---|---|---|---|
| 4,646,241 | 2/1987 | Ratchford et al. | |
| 5,714,678 | 2/1998 | Jurcik et al. | 73/31.03 |
| 5,742,399 | 4/1998 | McAndrew et al. | 356/437 |
| 5,835,230 | 11/1998 | McAndrew et al. | 356/437 |

FOREIGN PATENT DOCUMENTS

| | | |
|---|---|---|
| 2 174 261 | 2/1986 | United Kingdom . |
| WO89/12279 | 12/1989 | WIPO . |

OTHER PUBLICATIONS

May et al, "Data Processing and Calibration for Tunable Diode Laser Harmonic Absorption Spectrometers," *Journal of Quantitative Spectroscopy,* vol. 49, No. 4, 1993, pp. 335–347.

Webster et al, "Aircraft (ER–2) Laser Infrared Absorption Spectrometer (ALIAS) for In–Situ Stratospheric Measurements of HCl, N₂O, CH₄, NO₂, and HNO₃," *Applied Optics,* vol. 33, No. 3, Jan. 20, 1994, pp. 454–472.

Nguyen, Bentz, and Byrd; "Methods for Measuring Water Diffusion in a Coating Applied to a Substrate": Jounal of Coatings Technology; vol. 67, No. 844, pp. 37–46, May 1995.

News Release; "ESCO Silicone Rubber used in the Novel membrane Inlet Mass Spectrometry Technique"; p. 11, May 22, 1987.

*Primary Examiner*—James P. Trammell
*Assistant Examiner*—Demetra R. Smith
*Attorney, Agent, or Firm*—Burns, Doane, Swecker & Mathis, L.L.P.

[57] ABSTRACT

Provided is a novel method for intelligent data acquisition in a measurement system. The method comprises the following steps: (a) providing a measurement system; (b) performing a measurement with the measurement system, thereby obtaining a measurement result; (c) writing the measurement result to a data file on a first storage device; (d) repeating steps (b) and (c) one or more times, thereby accumulating a plurality of measurement results in the data file; (e) generating one or more summary values from the measurement results; (f) saving the one or more summary values to a summary file on the first storage device or on a second storage device; (g) comparing at least one of the one or more summary values with a respective predefined standard summary value corresponding to the at least one summary value, wherein the comparing is made on the basis of a predefined inequality for each summary value being compared; and (h) saving the data file to the first storage device, the second storage device, or a third storage device if one or more of the at least one summary values compared in step (g) is outside of an acceptable range as defined by the respective inequalities, and/or optionally, when a trigger indicates that a condition is present. Particular applicability is found in in-situ moisture concentration measurement in a semiconductor processing apparatus.

16 Claims, No Drawings

METHOD FOR INTELLIGENT DATA ACQUISITION IN A MEASUREMENT SYSTEM

BACKGROUND OF THE INVENTION

1. Field of the Invention

The present invention relates to a novel method for intelligent data acquisition for a measurement system. The method has particular applicability in intelligent data acquisition from a system which can be used to monitor a semiconductor processing tool.

2. Description of the Related Art

Large volumes of data tend to be generated in on-line measurement systems, leading to significant difficulties in data handling and data acquisition. For example, in the field of in-situ particle monitoring, used widely in the semiconductor manufacturing industry, a particle counter is often incorporated into or added to the exhaust line of a semiconductor processing tool. Particles in the exhaust line are then counted continuously, and the measured particle counts are used as an indicator of the quality of the semiconductor manufacturing process. Full utilization of the particle measurements, however, is often hampered by the sheer volume of data accumulated. This is compounded by the difficulty in correlating particle counts in the exhaust line with defects on the product wafers.

In-situ monitoring of moisture in the semiconductor manufacturing industry is a relatively new field. This method is of particular interest since moisture is generally considered a more useful indicator of the extent of contamination in a semiconductor processing tool than are particle monitoring systems. Although in-situ moisture monitoring is a much newer field than in-situ particle monitoring, field trials have revealed that the problems associated with the handling of large quantities of data in particle monitoring are also encountered with moisture monitoring.

The concentration of the gas species being measured can be calculated based on the results of the absorption measurement together with the sample pressure, the sample temperature, the length of the diode laser light path and the nature of the gas species present. This calculation is well known, and is described, for example, by R. D. May and C. R. Webster, *Journal of Quantitative Spectroscopy and Radiative Transfer,* Vol. 49(4), pp. 335–347 (1993).

Data collection from a diode laser system may be automated as described by C. R. Webster et al, *Applied Optics* Vol. 33(3), pp. 454–472 (1994). Although this publication and the previously mentioned publication are concerned with airborne measurement of atmospheric components, the same electronics and data processing can be applied to in-situ moisture monitoring. The primary difference between the two methods lies in the timing of the calculations following measurement. In the airborne measurement of atmospheric components, multiple spectra are collected during flight followed by moisture concentration determination. Because it is important that the data be more immediately available for in-situ moisture monitoring, it is necessary that moisture concentrations be calculated directly after the measurement of each spectrum.

The output from the in-situ moisture sensor is a record of moisture concentration versus time, with the interval between moisture concentration measurements typically being in the range of from about one to three seconds. Because the in-situ sensor is often operated unattended for days or weeks at a time, a large volume of data can rapidly accumulate over that time period.

In a typical data collection system, moisture concentration and several other diagnostic parameters are written to a file on a memory storage device, called a "data file." At predefined intervals of, for example, 20 minutes, the currently open data file is saved and closed, and a new data file is opened. Although the period corresponding to data collection for a given data file can be longer, this period is generally set at less than one hour due to limitations of memory encountered and the risk of losing large blocks of data in the event a data file is corrupted. The data file is assigned a name which is generated automatically, for example, according to the date and time at which it is saved.

According to a procedure currently in use in many data acquisition systems, and in particular, in unattended diode laser systems, a signal to save and close the currently open data file and to open a new data file is sent to the measurement system after a counter reaches some predefined number. This counter is incremented by one each time a new moisture concentration is calculated and the corresponding record is written to the data file.

In these continuously operating measurement systems, it is necessary to examine all of the data collected for proper analysis of the process which is being monitored. Although various aspects of the data collected can be readily automated (e.g., by data charting), the data review task remains very time consuming.

In addition, depending upon the utilization of the processing tool with which the moisture sensor is associated, the importance of different blocks of data collected can vary widely. A known solution to the above-described problem, used in the field of in-situ particle counting, is to provide a trigger to the measurement system whenever the processing tool becomes active. The measurement system then operates only after becoming activated by the trigger, i.e., during actual operation of the processing tool. One disadvantage of this solution is the inability to collect data when the processing tool is inactive, thereby preventing the collection of baseline data. Moreover, a compatible output from the processing tool is required to provide the measurement system with such a trigger. Because compatible outputs are sometimes lacking, a trigger is often unavailable. Finally, this solution does not reduce the total amount of data collected during processing, nor does it do anything to increase utilization of that data.

To overcome the disadvantages of the prior art, it is an object of the present invention to provide a novel method for intelligent data acquisition in a measurement system, which method can substantially reduce the size of the data storage system called for, as well as the time required for review of the collected data. The inventive method further eliminates the need for a compatible output signal from a semiconductor processing tool.

SUMMARY OF THE INVENTION

According to a first aspect of the present invention, a method for intelligent data acquisition in a measurement system is provided. The method comprises the following steps:

(a) providing a measurement system;
(b) performing a measurement with the measurement system, thereby obtaining a measurement result;
(c) writing the measurement result to a data file on a first storage device;
(d) repeating steps (b) and (c) one or more times, thereby accumulating a plurality of measurement results in the data file;

(e) generating one or more summary values from the measurement results;

(f) saving the one or more summary values to a summary file on the first storage device or on a second storage device;

(g) comparing at least one of the one or more summary values with a respective predefined standard summary value corresponding to the at least one summary value, wherein the comparing is made on the basis of a predefined inequality for each summary value being compared; and (h) saving the data file to the first storage device, the second storage device, or a third storage device if one or more of the at least one summary values compared in step (g) is outside of an acceptable range as defined by the respective inequalities, and/or optionally, when a trigger indicates that a condition is present.

According to a second aspect of the invention, the measurement system performs an in-situ measurement of a gas phase molecular species in a gas passing through a sample region. This method is similar to that described above, except that the measurement results are concentration measurements.

The objects and advantages of the invention will become apparent from the following detailed description of the preferred embodiments thereof.

DETAILED DESCRIPTION OF THE PREFERRED EMBODIMENTS OF THE INVENTION

The above objectives of the present invention have been realized through the use of a method for intelligent data acquisition. While not being limited thereto, the method finds particular applicability in the performance of an in-situ measurement of a gas phase molecular species in a semiconductor processing tool.

In particular, while the following description is made with reference to the measurement of gas phase molecular species, and specifically to moisture (i.e., water vapor) concentration measurements, the method according to the invention can equally be applied to any measurement system in which data is periodically collected.

As used herein, the term "gas phase molecular species" refers to a molecular gas or vapor species which is the object of the measurement.

In the case of concentration measurement by tunable diode laser absorption spectroscopy (TDLAS), a number of species other than water vapor can be detected. For example, nitric oxide, carbon monoxide and methane or other hydrocarbons can be detected, subject only to the availability of a suitable light source.

In the data acquisition method of the invention, the measurement system can include a fast moisture sensor using a tunable semiconductor diode laser incorporated into the exhaust line of a semiconductor processing tool. Examples of suitable processing tools include an ion implantation apparatus, a sputtering apparatus, a rapid thermal processing apparatus and a chemical vapor deposition (CVD) apparatus. The diode laser, tuned to emit light at a particular wavelength which corresponds to an absorption characteristic of the gas phase species of interest, transmits the light beam into the sample region in the exhaust line. The light transmitted through the sample is measured by a detector, such as a photodiode, thereby detecting the molecular species in the gas passing through the sample region.

After each measurement, the concentration of the molecular species is calculated, and the concentration value for that measurement is written to a data file on a storage device, which data file accumulates the concentration values. Suitable storage devices are known in the art and include, but are not limited to, magnetic storage media and even memory on the microchip level.

After a predefined period of time, or after a predefined number of measurements (e.g., concentration measurements), measurement values have been written to the data file, one or more summary values are generated and written to a second file, called a summary file. The summary file can be located on the same storage device on which the data file is located, or optionally, on a separate storage device. The one or more summary values can include any statistical function. For example, in the case of concentration measurements, one or more of the following statistical functions (or others) may be of interest: the mean concentration $\bar{x}$; the maximum concentration $x_{max}$; and the standard deviation $\sigma$ of the concentration values accumulated in the data file. The summary values for subsequent data files are cumulatively stored in the summary file.

The current summary file is saved and closed, and a new summary file is opened after a predefined period of time has passed or after a predefined number of data files have been summarized. The use of relatively long time intervals between consecutive summary files is possible. Even with a large number of data files, a time interval of, for example, 24 hours can be used.

According to the inventive method, one or more of the summary data from each data file is examined to determine whether or not the data file upon which the summary data is based should be saved to a storage device or deleted. As a result, only those data files of interest are saved, thereby reducing the amount of memory required for data storage.

The summary data in the summary file is examined according to a smart data saving algorithm. This algorithm allows for the employment of user-defined criteria, by which a logical determination can be made as to whether or not the data file itself or only the summary data corresponding to that data file should be saved to a memory storage device.

According to the method of the invention, one or more of the summary values calculated for a given data file are compared with predefined standard values which corresponds to that particular summary values. Depending on how the algorithm is set up, if any one or a combination of the summary values is outside of an acceptable range as defined by the respective inequalities, the data is of interest and the data file is saved.

Additional to or instead of the standard value comparison, if a trigger indicates that some condition is present, for example, that the processing tool is in process, the data file can also be saved.

In an exemplary method in accordance with the invention, an absorption spectroscopy measurement system is provided for the measurement of moisture concentration in a semiconductor processing tool.

The summary values calculated include the mean concentration $\bar{x}$, the maximum concentration $x_{max}$, and the standard deviation $\sigma$ of the moisture concentrations included in the data file. The summary file is opened, and, for ease of data review, a line is written to the summary file which includes the time, the name of the corresponding data file upon which the summary values are based, and the summary values for that data file. If a trigger is being used to indicate the status of the processing tool, then the data line can also include a field indicating whether the processing tool was in process during any period of time corresponding to the data file.

If one or more of the summary values, in this case, the mean $\bar{x}$, the maximum concentration $x_{max}$, or the standard deviation $\sigma$ of the moisture concentration does not satisfy the following inequality with respect to its corresponding predefined standard value, $\bar{x}_s$, $x_{max-s}$, or $\sigma_s$, respectively, and there is no indication received from a trigger that processing has occurred, then the corresponding data file is not saved:

$$\bar{x} \geq \bar{x}_s$$

$$x_{max} \geq x_{max-s}$$

$$\sigma \geq \sigma_s$$

Conversely, if any one of the summary values satisfies the above inequality, or if a trigger indicates that the processing tool was in operation for at least a portion of the period corresponding to the data file, that data file is saved to the data storage device.

Of course, the standard values selected and the inequalities used are not limited to the above, but will depend on the specific type of measurement system and will be application specific.

The predefined moisture concentration standard values which determine whether or not the data file is to be saved are selected based on the detection limit and/or the baseline moisture levels of the processing tool. For example, if a sensor which has a background level of 200 ppb moisture and a sensitivity (3 standard deviations of the baseline signal) of 150 ppb is connected to the exhaust line of a semiconductor processing tool which is then established to have a moisture content of between 500 and 800 ppb moisture in the exhaust line even when no wafer processing is taking place, reasonable values for the mean $\bar{x}$, the maximum concentration $X_{max}$, and the standard deviation $\sigma$ values are, for example, 700, 1000 and 100 ppb, respectively.

Provided that the moisture is indeed detectable at some point during processing at intervals less than the period corresponding to the data file, a dedicated trigger indicating that processing is occurring is rendered unnecessary. In the event that moisture is only detectable at certain times during processing, the period during which the concentration values are written to the data file can be adjusted to avoid losing important measurements.

The aim of the above embodiment of the invention is to eliminate the need to analyze and store data files when the processing tool is inactive and if no other significant moisture event occurs, while still capturing a sufficient record of the background moisture behavior to establish a baseline.

Further and more sophisticated embodiments of the invention can be established by the inclusion of a greater number of parameters in the summary file. Examples of additional parameters which can be expected to be of interest include the number of local maxima, and the number of data points with moisture concentrations greater than certain predefined levels. These embodiments can be used, for example, to provide a preliminary analysis of actual processing records, once the typical moisture behavior during the processes of interest has been sufficiently characterized.

While data files are generally not saved for periods during which the processing tool is inactive, the tool baseline can easily be established from the summary values for those periods which are recorded in the summary file. However, in the event a moisture event does take place while the processing tool is inactive, as may occur during maintenance of the processing tool, the event will be recorded in full detail. This characteristic renders unnecessary the need for a compatible output signal from the processing tool.

As a consequence of the intelligent data acquisition method according to the invention, the total number of data files which must be saved can be drastically reduced compared to other measurement/data acquisition methods. Consequently, capacity of the data storage system as well as the time required for review of the measured data can be significantly reduced. Moreover, the inventive method can aid in reducing the time to react to potential yield affecting events taking place in the processing tool. This can result in large cost savings due to reductions in the extent of product loss from such events. Use of a summary file in accordance with the invention enables preliminary screening of data collected during processing by comparing the summary parameters with values known to be typical of the process. Thus, only the most interesting or anomalous data need be examined in detail.

While the invention has been described in detail with reference to specific embodiments thereof, it will be apparent to one skilled in the art that various changes and modifications can be made, and equivalents employed, without departing from the scope of the appended claims.

What is claimed is:

1. A method for intelligent data acquisition in a measurement system, comprising:
    (a) providing a measurement system;
    (b) performing a measurement with the measurement system, thereby obtaining a measurement result;
    (c) writing the measurement result to a data file on a first storage device;
    (d) repeating steps (b) and (c) one or more times, thereby accumulating a plurality of measurement results in the data file;
    (e) generating one or more summary values from the measurement results;
    (f) saving the one or more summary values to a summary file on the first storage device or on a second storage device;
    (g) comparing at least one of the one or more summary values with a respective predefined standard summary value corresponding to the at least one summary value, wherein the comparing is made on the basis of a predefined inequality for each summary value being compared;
    (h) saving the data file to the first storage device, the second storage device, or a third storage device if one or more of the at least one summary values compared in step (g) is outside of an acceptable range as defined by the respective inequalities, and/or optionally, when a trigger indicates that a condition is present.

2. The method for intelligent data acquisition according to claim 1, further comprising the step of:
    (i) repeating steps (b) through (h) one or more times n for n additional data files.

3. The method for intelligent data acquisition according to claim 1, wherein the summary file is closed and a new summary file is opened after a predefined interval of time.

4. The method for intelligent data acquisition according to claim 1, wherein the measurement system is an absorption spectroscopy measurement system.

5. The method for intelligent data acquisition according to claim 4, wherein the measurement result is concentration of a molecular gas phase species.

6. The method for intelligent data acquisition according to claim 5, wherein the molecular gas phase species is water vapor.

7. The method for intelligent data acquisition according to claim 1, wherein the sample region is located in a process chamber of or an exhaust line of a semiconductor processing tool.

8. The method for intelligent data acquisition according to claim 1, wherein the measurement system is an absorption spectroscopy measurement system.

9. The method for intelligent data acquisition according to claim 8, wherein the measurement result is concentration of a molecular gas phase species.

10. The method for intelligent data acquisition according to claim 1, wherein the data file is saved in step (h) when the trigger indicates that the semiconductor processing tool is in process.

11. A method for intelligent data acquisition in a measurement system, comprising:
   (a) providing a measurement system for performing an in-situ measurement of a gas phase molecular species in a gas passing through a sample region;
   (b) measuring an absorption for the molecular species and calculating a concentration thereof with the measurement system;
   (c) writing the concentration to a data file on a first storage device;
   (d) repeating steps (b) and (c) one or more times, thereby accumulating a plurality of concentration results in the data file;
   (e) generating one or more summary values from the concentration results;
   (f) saving the one or more summary values to a summary file on the first storage device or on a second storage device;
   (g) comparing at least one of the one or more summary values with a respective predefined standard summary value corresponding to the at least one summary value, wherein the comparing is made on the basis of a predefined inequality for each summary value being compared;
   (h) saving the data file to the first storage device, the second storage device, or a third storage device if one or more of the at least one summary values compared in step (g) is outside of an acceptable range as defined by the respective inequalities, and/or optionally, when a trigger indicates that a condition is present.

12. The method for intelligent data acquisition according to claim 11, further comprising the step of:
   (i) repeating steps (b) through (h) one or more times n for n additional data files.

13. The method for intelligent data acquisition according to claim 11, wherein the summary file is closed and a new summary file is opened after a predefined interval of time.

14. The method for intelligent data acquisition according to claim 11, wherein the molecular gas phase species is water vapor.

15. The method for intelligent data acquisition according to claim 11, wherein the sample region is located in a process chamber of or an exhaust line of a semiconductor processing tool.

16. The method for intelligent data acquisition according to claim 11, wherein the data file is saved in step (h) when the trigger indicates that the semiconductor processing tool is in process.

* * * * *